United States Patent
Trakumas et al.

(10) Patent No.: US 7,334,453 B2
(45) Date of Patent: Feb. 26, 2008

(54) MODULAR PARTICULATE SAMPLER

(75) Inventors: Saulius Trakumas, Pittsburgh, PA (US); Donald Lee Smith, West Newton, PA (US); Charles W. Nachreiner, Pittsburgh, PA (US); Peter M. Hall, Venetia, PA (US)

(73) Assignee: SKC, Inc., Eighty Four, PA (US)

( * ) Notice: Subject to any disclaimer, the term of this patent is extended or adjusted under 35 U.S.C. 154(b) by 132 days.

(21) Appl. No.: 11/213,528

(22) Filed: Aug. 26, 2005

(65) Prior Publication Data

US 2007/0044577 A1    Mar. 1, 2007

(51) Int. Cl.
*G01N 1/00* (2006.01)
*G01N 1/24* (2006.01)

(52) U.S. Cl. .................. 73/28.05; 73/28.01; 73/28.04; 73/863.22

(58) Field of Classification Search .............. 73/28.01, 73/28.04, 28.05, 28.06, 863.22
See application file for complete search history.

(56) References Cited

U.S. PATENT DOCUMENTS

| | | | |
|---|---|---|---|
| 3,693,457 A * | 9/1972 | Pilat | .................... 73/865.5 |
| 3,957,469 A | 5/1976 | Nebash | |
| 3,966,439 A | 6/1976 | Vennos | |
| 3,983,743 A * | 10/1976 | Olin et al. | .................. 73/28.06 |
| 4,321,822 A * | 3/1982 | Marple et al. | ............. 73/28.06 |
| 4,640,140 A | 2/1987 | Burghoffer et al. | |
| 4,675,034 A | 6/1987 | Lynch et al. | |
| 4,796,475 A | 1/1989 | Marple | |
| 4,827,779 A | 5/1989 | Marple et al. | |
| 4,972,957 A * | 11/1990 | Liu et al. | ..................... 209/143 |
| 5,040,424 A | 8/1991 | Marple et al. | |
| 5,333,511 A | 8/1994 | Boyum et al. | |
| 5,404,762 A | 4/1995 | Rodgers et al. | |
| 5,437,198 A | 8/1995 | John | |
| 6,101,886 A * | 8/2000 | Brenizer et al. | ......... 73/863.23 |
| 6,692,553 B2 | 2/2004 | Jordan, Sr. et al. | |

* cited by examiner

*Primary Examiner*—Daniel S. Larkin
(74) *Attorney, Agent, or Firm*—Beck & Thomas, P.C.

(57) ABSTRACT

A gas sampler includes an impact disc for removing larger particles from a gas flow drawn by a pump and a filter for capturing smaller particles, also positioned in the flow path. The sampler is conveniently dissembled and reassembled to remove and replace the impact disc and the filter. Particles removed, especially on the filter, may be observed or analyzed. The impact disc may be coated with an oil or other viscous substance to enhance its ability to retain larger particles. The flow path may be entirely annular after striking the impact disc—that is, around the outside of the impact disc but a portion of the flow path may proceed directly through a central aperture in the impact disc after striking it.

12 Claims, 4 Drawing Sheets

MODULAR PARTICULATE SAMPLER

TECHNICAL FIELD

A device for collecting particulates from air and other gases comprises a disposable impact disc and a filter downstream therefrom, the impact disc and filter being held in a readily dissembled and reassembled modular sequence. The air or other gas typically is moved through the collector at about ten liters per minute, and larger particles are collected on the impact disc while the smaller particles, generally desired as a sample for analysis or observation, are collected on the filter. Both the impact disc and the filter can be readily replaced.

BACKGROUND OF THE INVENTION

The reader may be interested in the following U.S patents, which describe various air samplers, particulate collectors, and the like: Burghoffer et al. U.S. Pat. No. 4,640,140, Marple et al. U.S. Pat. No. 4,796,475, Jordan, Sr. et. al . U.S. Pat. No. 6,692,553, John U.S. Pat. No. 5,437,198, Rodgers et al. U.S. Pat. No. 5,404,762, Marple et al. U.S. Pat. No. 5,040,424, Vennos U.S. Pat. No. 3,966,439, Lynch et al. U.S. Pat. No. 4,675,034, Marple et al. U.S. Pat. No. 4,827,779, and Nebash U.S. Pat. No. 3,957,469.

There is a demand for a portable, easily deployable, particulate matter sampler, for removing particulates from the air for inspection and analysis, especially particulates in the range of 0.1 to 100 μm in aerodynamic diameter, and typically below 10 μm aerodynamic diameter. Larger particles need to be screened or otherwise removed efficiently ahead of the filter in order to provide a clean collection of particles of the required size on the filter. Air flow is achieved by a pump chosen for the purpose, i.e. to draw air through the sampler at a rate of ten liters per minute, more or less; the pump may be battery operated so the sampler can be deployed in a somewhat remote area if desired, or so the sampler may be used to assess personal exposure.

Ideally the device will be easily dissembled so the filter and any member used for collecting larger particles (such as an impact disc having an adhesive coating) can be removed, observed, analyzed, and/or disposed of, while the filter and the impact disc may be replaced easily.

SUMMARY OF THE INVENTION

We have invented a particulate sampler that is simple and can be easily deployed, and which can be readily dissembled so the filter can be replaced, the large particle separator can be replaced, and the unit returned to service in a very short time, while the particle collections are taken to a laboratory or other facility for examination.

Our invention includes a device for collecting a sample of particulates from a gas, usually air, comprising (a) a housing including an inlet member and an outlet member for the gas and defining a flow path for the gas from the inlet member to the outlet member, the inlet member and the outlet member being normally attached to each other but readily separable, (b) a particle collecting assembly within the housing, the particle collecting assembly including a substantially planar particle impact disc, a support for the particle impact disc, a filter, and a support for the filter, the impact disc being situated substantially orthogonal to the flow path and including an adhesive coating, whereby particulates in the gas may impact on the impact disc and be retained thereon, the impact disc resting on the support for the impact disc and readily removable therefrom when the inlet member and the outlet member are separated, the filter resting on the filter support and being readily removable therefrom when the inlet member and the outlet member are separated, the filter being situated substantially orthogonal to the flow path and downstream in the flow path from the impact plate.

DETAILED DESCRIPTION OF THE INVENTION

Figure 1:
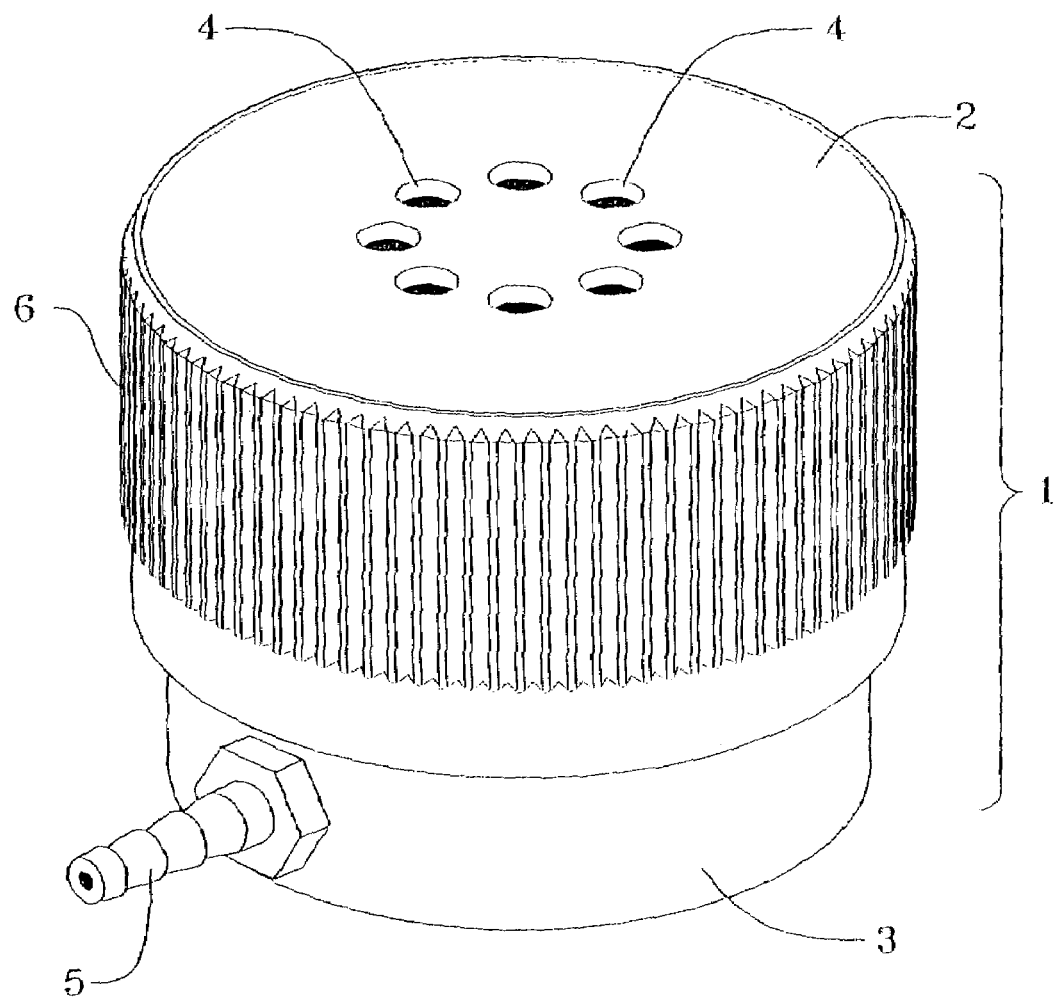
FIG. 1 shows the outside of our sampler, fully assembled.

Referring now to FIG. 1, the housing 1 comprises an inlet member 2 and an outlet member 3, the inlet member 2 including apertures 4 for air or other gas to enter the housing and the outlet member 3 having an exit tube 5 for the air to exit the sampler after having its particulate matter removed to the extend intended, more or less. The inlet member 2 may include roughened area 6 to facilitate manually turning the inlet member to mate the threads not shown under its sides with a threaded area (see FIG. 2, item 22) on the outlet member 3, thus compressing the O-rings 10 and 21 between filter capsule top 16 and bottom 11 (see FIG. 2) and effecting seals for the gas flow path (see the arrows in FIG. 3). As the device can be left unattended in a more or less remote area, it may be desirable to protect the inlet member 2 from rain. This may be accomplished in any manner which does not adversely affect the flow of air into the inlet member 2. As is known in the art, the exit tube is typically connected to an air pump to draw negative air pressure on the exit tube so that a flow path will be established through the sampler flowing from the inlet member 2 to the outlet member 3. The device and the pump may be sized, for example, to collect particulates from an air flow of about ten liters per minute; however, we do not intend to be limited to any particular flow rate or dimensions for our sampler.

Figure 2:
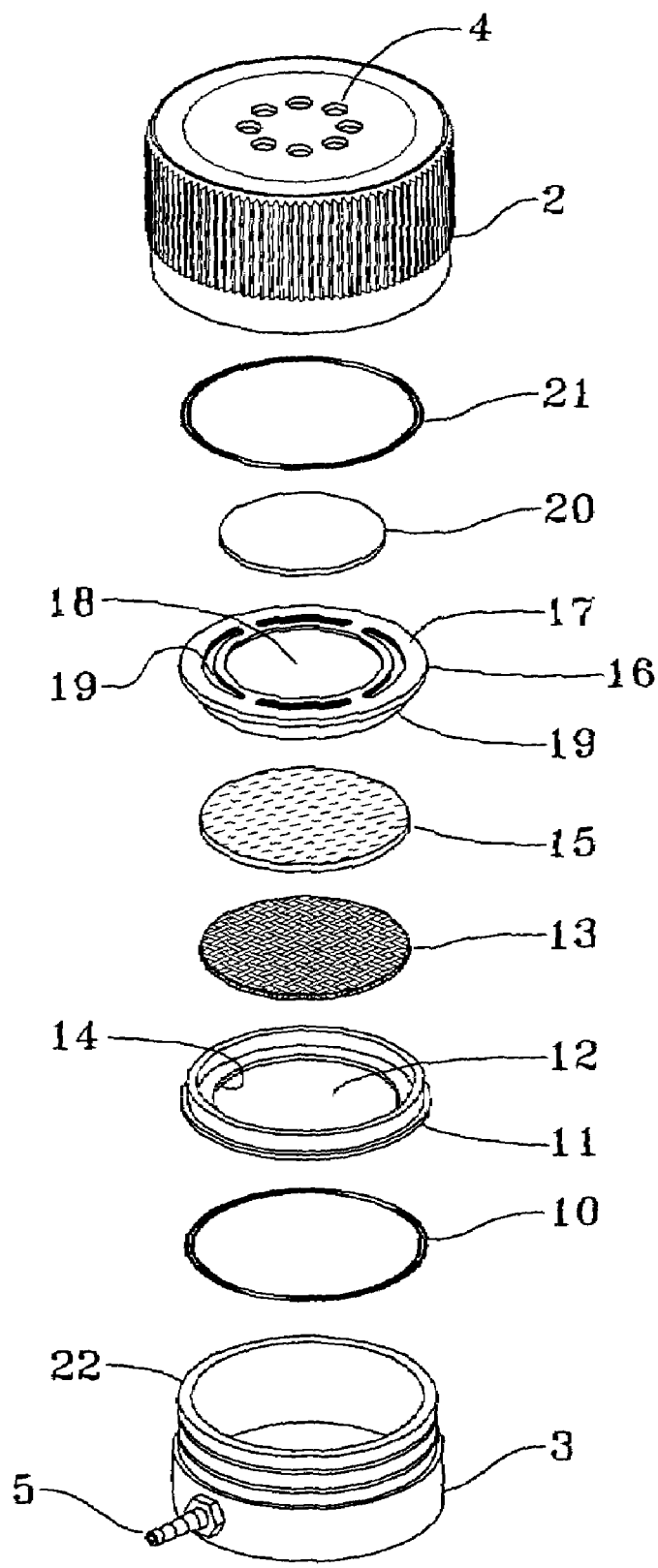
FIG. 2 is an exploded view of the sampler, showing the assembly of parts in spaced relation.

In FIG. 2, the internal components of the device are shown, forming a filter capsule with an incorporated impact disc. O-ring 10 will reside on outlet member 3, effecting a seal between the outlet member 3 and filter capsule bottom 11. Filter capsule bottom 11 has a large hole 12 in its center to facilitate air flow. Filter support 13, which in this case is a stainless steel screen, rests on lip 14 of filter capsule bottom 11. Set on top of the filter support 13 is the filter 15, selected for a desired permeability and retention abilities— that is, to retain the desired size of particulates while passing the air or other gas through. The filter capsule top 16 has an annular ledge 17 and a central support member 18, and defines a substantially annular passage 19. The particle impact disc 20, for example, a porous plastic disc soaked with silicone oil, will rest on the central support member 18 of the filter capsule top 16. An additional O-ring 21 will assure a seal between the inlet member 2 and filter capsule top 16 when the inlet member 2 and outlet member 3 are secured by threads 22, shown on the outlet member 3 but not visible on the inside surface of the inlet member 2.

Figure 3:
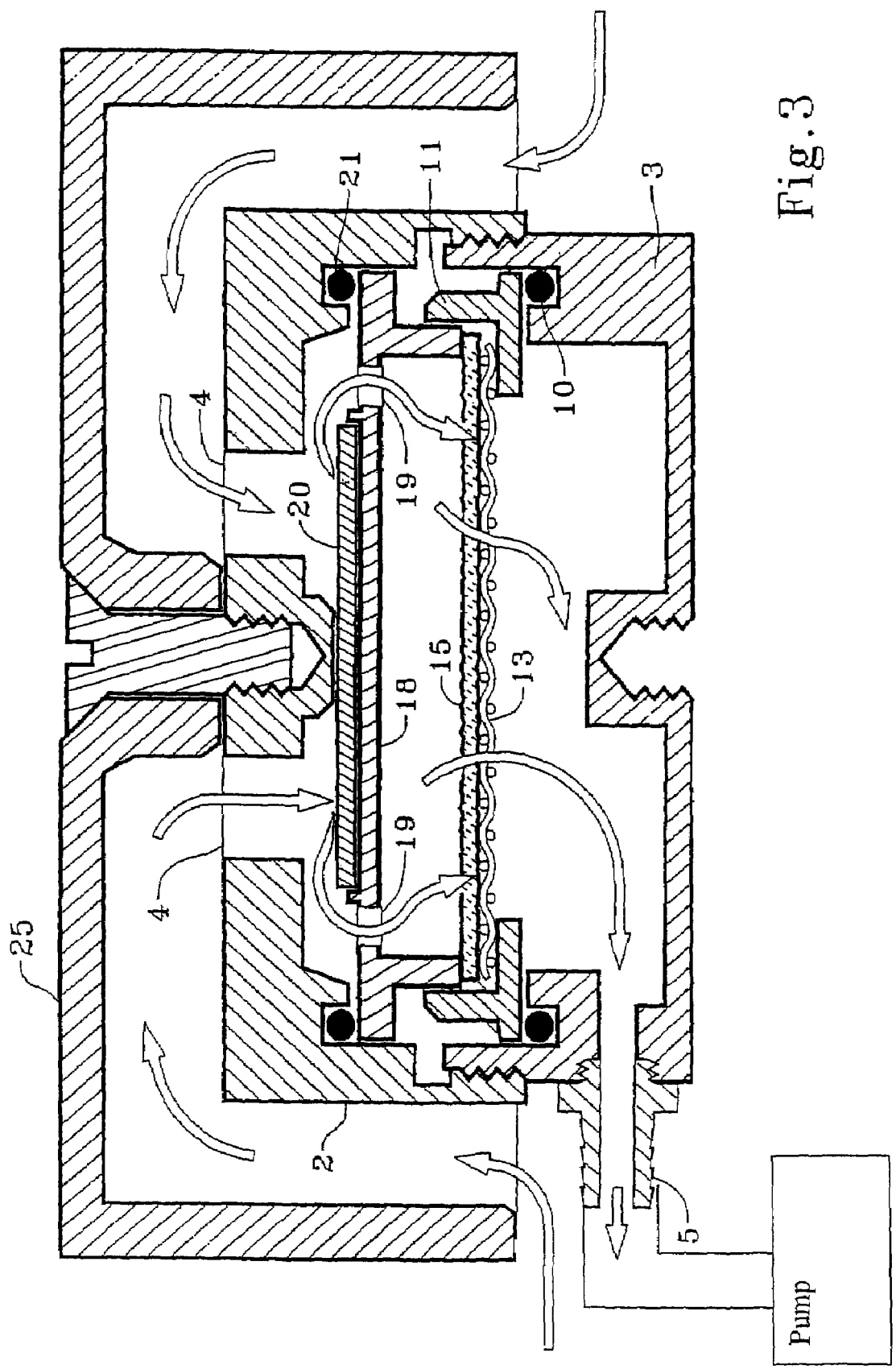
FIG. 3 is a sectional view of the assembled sampler, showing the gas flow path.
Figure 4:
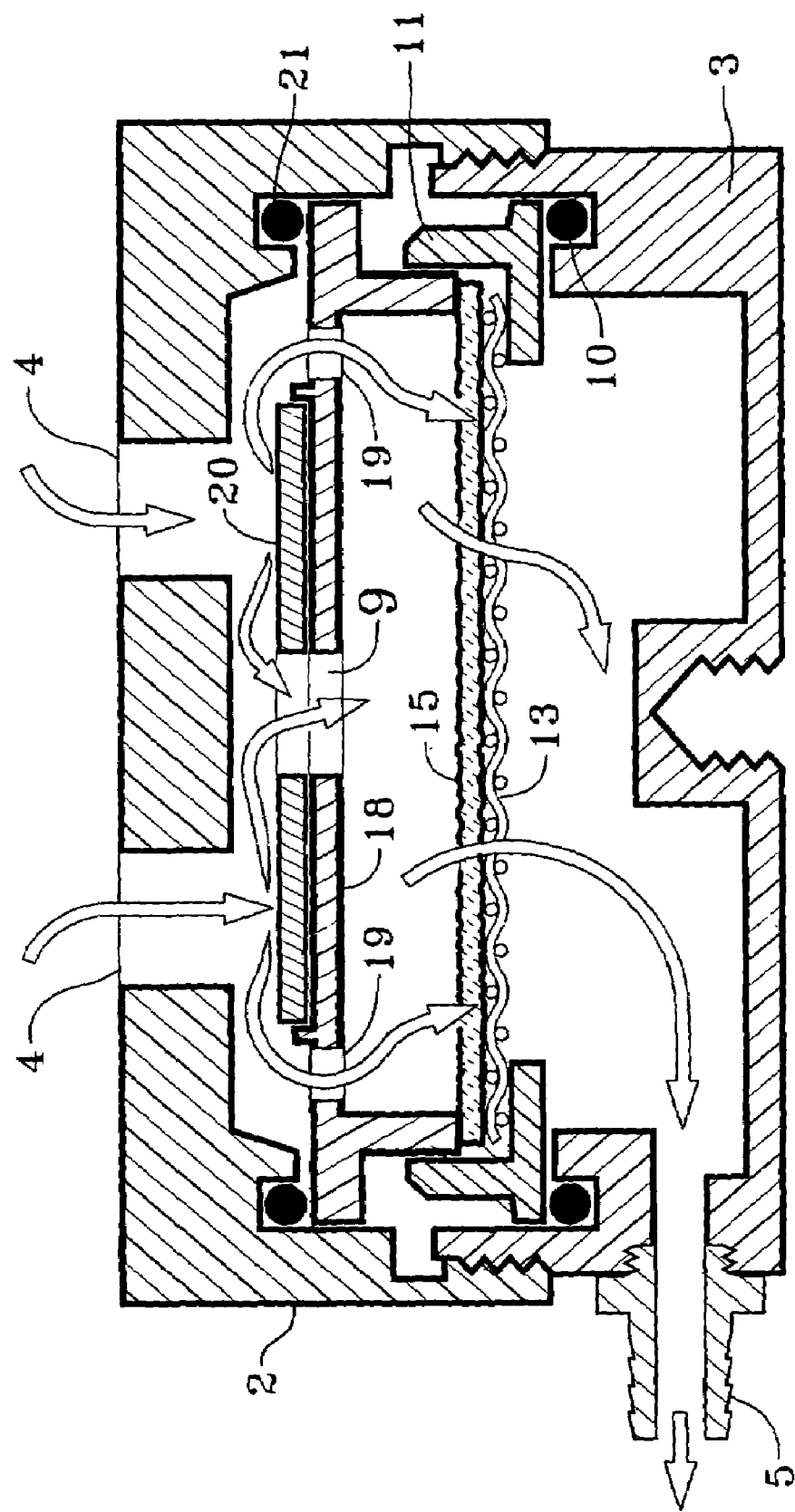
FIG. 4 is a variation of the sampler in which the impact disc has a central opening.

In FIG. 3, the assembled device is shown. The particle impact disc 20 is spaced from the apertures 4 in the inlet member 2 to achieve an air (or other gas) flow path as illustrated by the arrows. Initially the flow path is substantially downward, (orthogonal to the plane of the particle impact disc 20); the air encounters the particle impact disc 20, which causes it to flow outwardly and around the edges of the particle impact disc 20, carrying lighter particles (not shown) with it. Heavier particles will strike the particle impact disc 20 and remain there because of the adhesive characteristics of the surface of the particle impact disc 20, which may be enhanced by a coating of oil, viscous material, or other adhesive substance. After moving around the edges of the particle impact disc 20, the flow path encounters the filter 15, where particles not collected on impact disc 20 are deposited, being unable to pass through. There should be enough space between the central support member 18 and the filter 15 to permit significant air flow through the entire surface of the filter 15. That is, if the filter 15 is too close to the under side of the central support member 18, an undesirable restriction will distort the air flow and cause uneven particle deposition on filter 15, or result in an additional pressure drop which will in turn affect the air flow rate, further aggravating the problem, since a lower air flow than that for which the sampler was designed will, again, produce a separation at a different particle size than intended. Generally, the proportions of our dimensions and spaces are as follows. The distance from the inlet apertures 4 to the impact disc 20 should be 0.5 to 3.0 times the diameter of one aperture. The area of annular passage 19 should be no less than 1.5 times the total area of apertures 4. These dimensions will ensure high collection efficiency for particles larger than the cut off size onto impact disc and minimal losses of smaller particles from the filter.

The flow path proceeds through filter support 13, which is permeable or, in this case, a stainless steel screen having at least 30% open area for air to pass through without significant load on the pump. The air flow path then proceeds to the exit tube 5 and further to the pump, not shown, which is drawing the air through the entire apparatus.

FIG. 3 includes a weather protector 25 to reduce the likelihood of precipitation entering the apertures 4. Weather protector 25 may be secured to inlet member 2 in any satisfactory manner.

It should be observed that the particle impact disc 20 and its support 18, and the filter 15 together with its support 13 form a particle collecting assembly within the inlet and outlet members 2 and 3 of the housing 1. The particle collecting assembly, including filter capsule bottom 11 are available for almost instant replacement as a whole as soon as the housing is taken apart by unscrewing inlet and outlet members 2 and 3. That is, not only are the oiled disc 20 and filter 15 readily replaced, but the entire sampler can be returned to use as soon as the particle collecting assembly is removed, by simply replacing it with a new one. After the filter is removed for analysis and replaced, and the impact disc replaced, the particle collecting assembly, or module, is ready for a new deployment.

In operation and use, the pump may be battery operated and the device may be left unattended for some time. However, our sampler is designed so that the particle impact disc, and the filter, can be readily removed and replaced, and the unit returned to work in a very short time. In one version, size and number of apertures 4 and the distance between the apertures 4 and the particle impact disc 20 are chosen so that the separation between the larger particles captured on the particle impact disc 20 and the smaller ones captured on the filter 15 is at about 10 μm aerodynamic diameter when the air flow is 10 liters per minute. Other separations may be accomplished and other flow rates may be used, as will be apparent to persons skilled in the art.

It is to be understood that our invention is not limited to the specific illustrated versions. For example, we have illustrated eight apertures 4, but they may be varied in size, number, and location, as is known in the art, they can be rectangular or of other shapes rather than circular. Generally, the inlet apertures 4 should direct the incoming air or other gas towards the particle impact disc. As another example of variability, the particle impact disc may be of a shape somewhat different from circular, but the particle impact disc should be impervious and capable of stopping and retaining the larger particles which strike it owing to their inertia in the moving air; for this purpose the impact disc may be made of a material having at least some adhesive properties and/or may be coated with oil or other material that will enhance its ability to retain particles.

As seen in FIG. 4, particle impact disc 20 and the central support member 18 may have a central aperture 9 as well as an annular passage 19, provided that the apertures 4 are situated directly above the body of the impact disc and not above the central aperture of the disc or in a position not to cause the flow path to go around the impact disc. Thus, the arrows in FIG. 4 illustrate the air flow path through apertures 4, onto impact disc 20, and through both the annular passage 19 and the central aperture 9. The variation of FIG. 4 is otherwise more or less similar to that of FIG. 3, although in FIG. 4 there is no weather protector 25.

Another variation in the invention includes the possibility of employing various materials for the impact disc. These include quartz, fiber glass reinforced synthetic polymers, and TEFLON; generally any substrate capable of capturing and retaining larger particles expected to be encountered in the particular environment to be monitored.

Our invention includes a device as described wherein particles greater than 2.5 μm aerodynamic diameter are captured on the impact disc and particles smaller than 2.5 μm aerodynamic diameter are captured on the filter at a gas flow rate through the flow path of 10 L/minute. More generally, our invention includes a device for collecting a sample of particulates from a gas comprising (a) a housing including an inlet member and an outlet member for the gas and defining a flow path for the gas from the inlet member to the outlet member, the inlet member and the outlet member being normally attached to each other but readily separable, (b) a particle collecting assembly within the housing, the particle collecting assembly including a substantially planar particle impact disc, a support for the particle impact disc, a filter, and a support for the filter, the impact disc being situated substantially orthogonal to the flow path, whereby particulates in the gas may impact on the impact disc and be retained thereon, the impact disc resting on the support for the impact disc and readily removable therefrom when the inlet member and the outlet member are separated, the filter resting on the filter support and being readily removable therefrom when the inlet member and the outlet member are separated, the filter being situated substantially orthogonal to the flow path and downstream in the flow path from the impact plate.

What we claim is:

1. Device for collecting a sample of particulates from a flowing gas comprising:

(a) a housing including an inlet member and an outlet member for the gas and defining a flow path for the gas from the inlet member to the outlet member, the inlet member and the outlet member being normally attached directly to each other but readily separable; and (b) a particle collecting assembly within the housing, the particle collecting assembly including:
   (1) a substantially planar particle impact disc;
   (2) a filter;
   (3) a support member for supporting the particle impact disc, so that the impact disc is situated substantially orthogonal to the flow path and the flow path is directed around the circumference of the impact disc;
   (4) a capsule bottom for supporting the filter so that the filter is directly vertically below the impact disc so that the flow path flows vertically downward from the impact disc to the filter, the capsule bottom directly engaging the support member so that the particle collection assembly can be replaced as a single piece when the inlet member and outlet member are separated, thereby replacing both the filter and the impact disc in one step so that the entire sampler can be reused in as short amount of time as possible;
   the particle collecting assembly can be disengaged so that the filter and impact disc can be removed and replaced.

2. Device of claim 1 wherein said impact disc is situated substantially in the center of said flow path and wherein said flow path is thereby directed annularly around the periphery of said impact disc.

3. Device of claim 2 wherein said impact disc has an adhesive coating to enhance its ability to retain particulates.

4. Device of claim 3 wherein said adhesive coating on said impact disc is an oil.

5. Device of claim 1 wherein said impact disc includes a central aperture in its center.

6. Device of claim 1 wherein the capsule bottom has a large hole in its center and includes a steel screen within the hole to be used as a filter support so that the flow passes through the screen.

7. Device of claim 1 wherein said impact disc is disposable.

8. Device of claim 1 wherein said inlet member of said housing includes a plurality of symmetrically disposed apertures in said inlet member for said gas to enter said housing and approach said impact disc when gas is drawn through said inlet member and said outlet member.

9. Device of claim 8 wherein said apertures are sized to effect capture of particles greater than 10 .mu.m aerodynamic diameter on said impact disc and particles smaller than 10 .mu.m aerodynamic diameter on said filter at a gas flow rate through said flow path of 10 L/minute.

10. Device of claim 1 wherein particles greater than 2.5 .mu.m aerodynamic diameter are captured on said impact disc and particles smaller than 2.5 .mu.m aerodynamic diameter are captured on said filter at a gas flow rate through said flow path of 10 L/minute.

11. Device of claim 1 including a pump attached to said outlet member for drawing gas through said flow path.

12. Device for collecting a sample of particulates from a flowing gas comprising: (a) a housing including an inlet member and an outlet member for the gas and defining a flow path for the gas from the inlet member to the outlet member, the inlet member and the outlet member being normally attached to each other but readily separable, the inlet member having apertures; (b) a particle collecting assembly within the housing, the particle collecting assembly including a substantially planar particle impact disc, a support for the particle impact disc being located so that the distance from the apertures to the impact disc is 0.5 to 3.0 times the diameter of one aperture, the impact disc is situated substantially in the center of said flow path and the flow path is directed annularly around the periphery of the impact disc and through an annular passage, the annular passage is not less than 1.5 times the total area of the apertures, a filter, and a support for the filter, the impact disc being situated substantially orthogonal to the flow path, whereby particulates in the gas may impact on the impact disc and be retained thereon, the impact disc resting on the support for the impact disc and readily removable therefrom when the inlet member and the outlet member are separated, the filter resting on the filter support and being readily removable therefrom when the inlet member and the outlet member are separated, the filter being situated substantially orthogonal to the flow path and downstream in the flow.

* * * * *